United States Patent [19]

Samuel et al.

[11] 4,127,939
[45] Dec. 5, 1978

[54] J-SHAPED PIN FOR MAKING DENTAL PROSTHESIS WITH MEANS FOR DEBRIS ESCAPE

[76] Inventors: Robert A. Samuel, 3603 Ethan Ct., San Jose, Calif. 95123; Gerald W. Kaminski, 760 Mansfield Dr., San Jose, Calif. 95128; Michael W. Layne, 112 Capistrano Dr., Los Gatos, Calif. 95030

[21] Appl. No.: 760,754

[22] Filed: Jan. 19, 1977

[51] Int. Cl.² ............................................. A61C 13/00
[52] U.S. Cl. ....................................................... 32/11
[58] Field of Search ................................... 32/11, 40 R

[56] References Cited

U.S. PATENT DOCUMENTS 4,054,995  10/1977  Yoshida ................................. 32/11

Primary Examiner—Robert Peshock

[57] ABSTRACT

In the making of fixed dental prosthesis, a model is employed, which is an accurate replica of the patient's teeth and gums. For reinforcement, the model is fixed to a base. A model comprises a replica of the teeth remaining in the patient's mouth and a replica of teeth to be prepared by restorative dentistry. For preparing the teeth by restorative dental techniques, a die is used. It is desired that the die be removed from and replaced in the model with facility, be indexed accurately relative to the model and have stability while positioned in the model against forces applied in the practice of prosthesis, and also be removable from the base on which the model is secured. Toward this end, a pin is fixed in the die having a locating leg and an indexing leg interconnected by an arcuate portion of the pin. The legs extend outwardly from the die to be received by the base to which the model is secured. A debris escape channel is formed in the base communicating with the opening in the base which receives the indexing pin to collect debris to reduce the tendency for debris to be disposed in the path of travel of the indexing pin into the base. Debris disposed in the path of travel of the indexing leg inhibits the full insertion or indexing movement of the indexing leg within the base.

9 Claims, 6 Drawing Figures

J-SHAPED PIN FOR MAKING DENTAL PROSTHESIS WITH MEANS FOR DEBRIS ESCAPE

BACKGROUND OF THE INVENTION

The present invention relates in general to models employed in restorative or prosthetic dentistry, and more particularly to an indexing pin and locating pin fixed in a removable die of a model and received by a base to which the model is secured.

In the making of a fixed dental prosthesis (i.e. gold and ceramic crown or bridge) it is required that an accurate replica of the existing teeth and gums (dentition) be made. The replicas, herein referred to as models, are made by taking an impression of dentition. Material capable of adapting to the exact shape and dimension of the dentition are, for example, silicon rubber and agar hydrocolloid. The impression is a "negative" model in which plaster, such as calcium sulfatehemihydrate, is poured. Upon removal from the impression, the plaster forms the model on which the prosthesis is constructed. The model is secured to a base of plaster to increase its overall strength.

The plaster model comprises teeth which are replicas of the teeth remaining in the mouth of the patient and a replica of the teeth to be prepared by prosthetic or restorative dentistry. It is the teeth prepared for the prosthesis to be developed upon that employs an indexing and locating pin.

The replica of the teeth to be prepared by prosthetic or restorative dentistry is known as a die. It is desirable in restorative dentistry that the die be removable from and replaceable in the model. Further, the die should be indexed in the model to reposition itself in all planes after removal. The replaced die should not vary or move from its original position in the model in any plane more than ±0.001 inch. Also, the die in its vertical removement from the model should be free to move in all planes immediately upon the vertical removal action to provide free play for removal of undercut or eccentric dies. The removal is in a direction perpendicular to the occular plane. Of course, the removal is from the base upon which the model is secured. While disposed in the model, the die should be retained in place as to be unyielding to the normal forces and pressures, for example torsion, that may be applied to it during the fabrication of the prosthesis. Thus, a die must be capable of being indexed in the model, must be removable with facility, and must be stable against forces applied thereto during the fabrication of the prosthesis.

In the patent to Robert A. Samuel et al. U.S. Pat. No. 3,952,415, issued on Apr. 27, 1976, for J-shaped Pin For Making Dental Prosthesis, there is disclosed a pin which is fixed in the die. The pin has a locating leg and an indexing leg interconnected by an arcuate portion of the pin. The legs extend downwardly from the die to be received by the base to which the model is secured.

It has been found that debris, such as plaster chips and dust, collects in the opening which receives the indexing leg. The debris is often generated by a technician cutting or grinding on the die or base. The collection of debris in the opening receiving the indexing leg inhibits or restricts the full insertion or indexing movement of the indexing leg. Such a restriction results in inaccuracies.

In the patent to Bernard Weissman, U.S. Pat. No. 3,153,283, issued on Oct. 2, 1964, for Dowel Pin Assembly For Dental Dies, there is disclosed a dowel comprising a dowel pin and a complementary dowel sleeve. The sleeve provides indexing for the dowel pin that is insertable in and removable from the dowel sleeve. The sleeve defines a bore disposed below and in alignment with the tip of the dowel pin.

SUMMARY OF THE INVENTION

An assembly for prosthetic dentistry in which a pin is fixed within a die and projects outwardly therefrom to be received by an opening in a base to which a model is secured and communicating with the opening is a debris escape channel formed in the base for collecting debris to reduce the tendency for debris to be disposed in the path of travel of the pin within the base. Debris in the path of travel of the pin inhibits the full insertion thereof within the base.

An assembly for prosthetic dentistry in which a pin fixed in a die has a locating leg and an indexing leg projecting from the die to be received by openings in a base to which a model is secured, and communicating with opening receiving the indexing leg is a debris escape channel formed in the base for collecting debris to reduce the tendency for debris to be disposed in the path of travel of the indexing leg within the base. Debris in the path of travel of the indexing leg inhibits the full insertion or indexing movement of the indexing leg within the base.

A method in the assembly of prosthetic dentistry in which a pin is disposed in a model of soft material with the free end of the pin projecting outwardly from the model at the location of a die. The model then solidifies with the free end of the pin projecting outwardly therefrom. A sleeve is disposed over the free end of the pin. A base is then applied to the model with the free end of the pin disposed therein, and the base then solidifies. The base is trimmed or formed of a prescribed depth to expose the end of the sleeve. The sleeve is removed from the base by a tool leaving a debris escape channel in communication with the free end of the pin.

A method in the assembly of prosthetic dentistry in which a pin having a locating leg and an indexing leg disposed in a model of soft material with the free ends of the legs projecting outwardly from the model at the location of a die. The model then solidifies with the free ends of the legs projecting outwardly therefrom. A sleeve is disposed over the free end of the indexing leg, which is the shorter of the legs, with the free end of the sleeve and the free end of the locating leg terminating at a point equi-distance from the model. A base is then applied to the model with the sleeve and the free ends of the locating leg and the indexing leg disposed therein. The base then solidifies. The base is trimmed or formed of a prescribed length to expose the sleeve and the free end of the locating leg. The sleeve is removed from the base by a tool, leaving a debris escape channel in communication with the free end of the indexing leg.

By virtue of the present invention, a debris escape channel collects the debris generated by the cutting or grinding on the die or base to reduce the tendency of debris being disposed in the path of travel of a pin or locating leg projecting from the die to be received by the base. As a consequence thereof, the full insertion of the pin or the indexing movement is not inhibited by the collection of debris from plaster chips or dust. Thus, the accuracy of the die being replaced in its original position in the model is increased in the vertical plane.

DESCRIPTION OF THE PREFERRED EMBODIMENTS

In prosthetic or restorative dentistry, a fixed dental prosthesis is fabricated, which may be gold or ceramic crown or bridge. This procedure requires an accurate replica of the existing teeth and gums. The existing teeth and gums are called dentition and the replica is called a model. Initially, an impression is made of the dentitions. Materials commonly employed for taking the impression are silicon rubber or agar hydrocolloid. The impression is a "negative" model in which plaster is poured, such as a wet technique, or a dry powder is employed, such as a dry technique. Upon removal from the impression, the plaster forms a model on which the prosthesis is constructed. The plaster hardens or solidifies prior to its use for the construction of the prosthesis.

Figure 1:
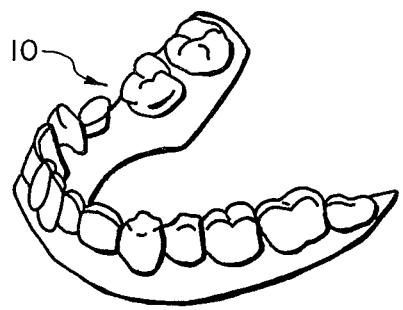
FIG. 1 is a perspective view of a model used in prosthetic or restorative dentistry.
Figure 4:
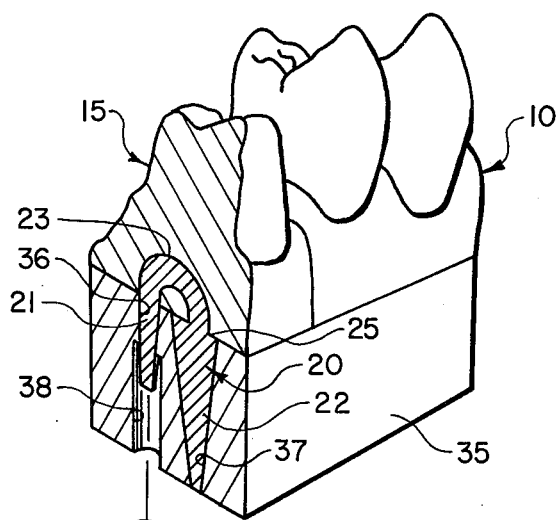
FIG. 4 is a diagrammatic view of the removal of the sleeve from the base.
Figure 5:
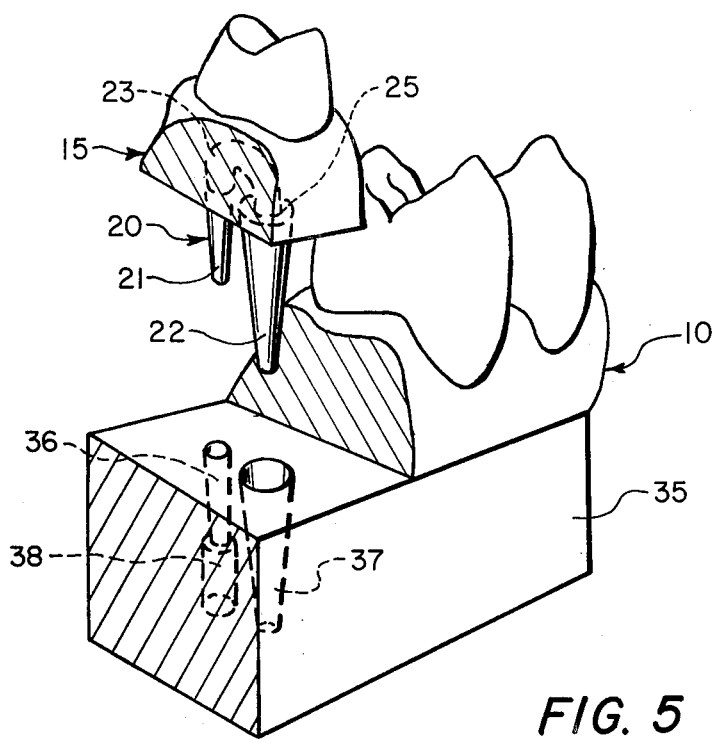
FIG. 5 is a fragmentary perspective view of the model shown in FIG. 3 with the sleeve thereof removed, leaving a debris escape channel and with the die of the model removed from the model.
Figure 6:
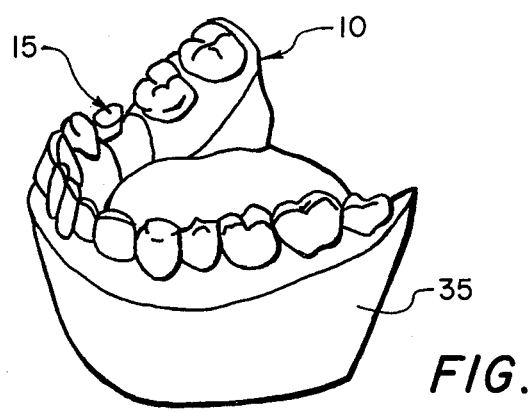
FIG. 6 is a perspective view of the model shown in FIG. 1 used in prosthetic or restorative dentistry secured to a base.

Illustrated in FIG. 1 is a plaster model 10, which is a replica of teeth remaining in the patient's mouth and a replica of teeth to be prepared by restorative or prosthetic dentistry. It is the replica of teeth from which a prosthetic restoration is prepared that embodies the present invention. The portion of the model 10 from which the prosthesis is to be developed on or fabricated from is a die 15 (FIGS. 4, 5 and 6).

Figure 2:
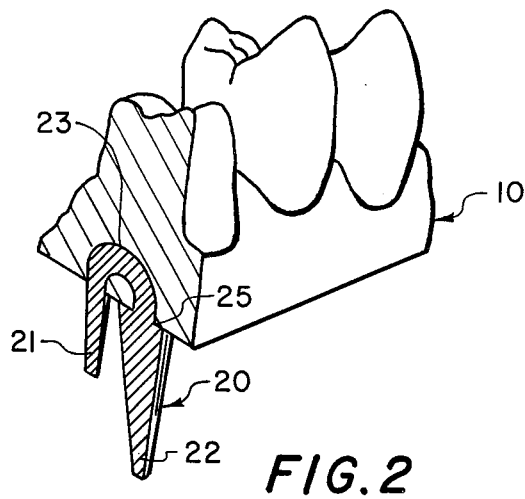
FIG. 2 is a fragmentary perspective view of the model shown in FIG. 1 with a pin disposed therein and with the free ends of the locating and indexing legs projecting outwardly therefrom.

In order to use the die 15 for prosthetic restoration, the die 15 must be removable from the model 10 and must be replaced in the model 10 (FIGS. 5 and 6) so as not to vary more than ±0.001 inch from its original position in any plane. As previously described, an impression of the patient's mouth is first made in the usual manner. Thereafter, the model 10 is cast from the impression and, when a slurry of plaster has been poured, a pin 20 (FIG. 2) is inserted into the plaster adjacent to the tooth recess or cavity before the plaster material has fully hardened or cured. The pin is inserted so that its orientation is generally perpendicular to the plane of occlusion.

The pin 20 (FIG. 2) comprises an indexing leg 21 and a locating leg 22. In the preferred embodiment, the pin 20 is made of a suitable metal, such as alloy 360 brass. Interconnecting the legs 21 and 22 to form an integral or unitary structure is an arcuate retention portion 23. It is the retention portion 23 that is embedded in the die 15 for improved retention of the pin 20 in the die 15. At the junction of the locating leg 22 and the retention portion 23 is a reduced diameter shoulder 25. The legs 21 and 22 along with the retention portion 23 form an inverted J-shape. The legs 21 and 22 of the pin 20 are contoured so that the legs 21 and 22, respectively, gradually decrease in cross-sectional area taken in the direction along the longitudinal axis thereof.

After the plaster of the model 10 has fully hardened with the pin 20 therein, a sleeve 30 (FIG. 3) is placed over the free end of the indexing leg 21 and extends therefrom. The sleeve 30, in the preferred embodiment, is a Teflon (TFE) tube. The free end of the sleeve 30 and the free end of the locating leg 22 project outwardly equi-distance from the lower wall of the model 10. Thus, the tips of the sleeve 30 and the locating leg 22 terminate in the same plane.

Additionally, after the plaster of the model 10 has fully hardened with the pin 20 therein, a separator medium, such as "Vasoline," is placed on the lower wall of the portion of the model 10 to form the die 15. Thereupon, additional plaster material is poured on or applied to the lower wall of the model 10 to form a base 35 (FIGS. 3–6). Thereupon, the base 35 and the model 10 are fully hardened and cured. The base 35 is generally made of the same material as the model 10, which is a plaster of calcium sulfatehemihydrate. It follows that the die 15 is also made of a plaster of calcium sulfatehemihydrate. The model 10 is secured to the base 35 for improved overall strength and the model 10 is fixed to the base 35 in a well-known manner by adhesion.

Figure 3:
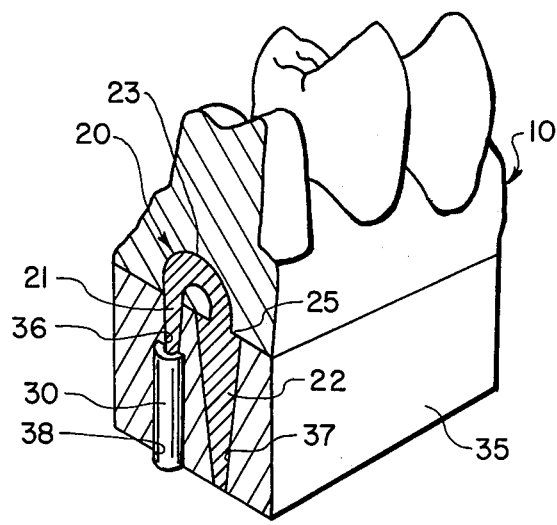
FIG. 3 is a fragmentary perspective view of the model shown in FIG. 2 with a base applied thereto and with a sleeve disposed on the free end of the indexing leg, the base receiving the locating leg, the indexing leg and the sleeve disposed on the indexing leg.

To form and to remove the die 15 from the model 10 (FIGS. 4 and 5), the model 10 is cut by a saw or the like along the sides of the die 15. The lower wall of the die 15 is separable through the separator medium. The legs 21 and 22 of the pin 20 form in the base 35 and are received by openings 36 and 37 so formed in the base 35. According to the present invention, the sleeve 30 also forms in the base 35 and is received by an opening 38 so formed in the base 35 which may be referred to as a debris escape channel 38 (FIGS. 3–5). Thus, the opening 36 conforms to the contour of the indexing leg 21, the opening 37 conforms to the contour of the locating leg 22, and the debris escape channel 38 conforms to the contour of the sleeve 30. The lower wall of the die 15 is disposed along the shoulder 25 of the pin 20.

The base 35 is either formed so that the lower wall thereof exposes the terminal ends of the sleeve 30 and the locating leg 22 or the lower wall of the base 35 is ground flat or is trimmed on a well-known dental model trimmer to expose the terminal ends of the sleeve 30 and the locating leg 22 (FIG. 3). At this time, the sleeve 30 is removed from the base 35 by means of a suitable tool T, such as a Hedstrom type, style B, #80 root canal file (FIG. 4). The tool T is screwed into the exposed end of the sleeve 30 by rotation about its axis and, when a sufficient engagement therebetween is made, the tool T is pulled away from the base 35 to remove the sleeve 30 therefrom. As a result thereof, the debris escape channel 38 is formed in the base 35, which communicates with the opening 36 that receives the indexing leg 21.

From the foregoing, it can be observed that the die 15 can be removed from the model 10 and replaced in the model 10 by reinserting the legs 21 and 22 of the pin 20 into the openings 36 and 37 of the base 35. The debris generated by an operator cutting or grinding on the die 15 or the base 35 is collected in the debris escape channel 38. The consequence thereof is to reduce the tendency of debris to collect in the path of travel of the indexing leg 21. The collection of debris in the path of travel of the indexing leg 21 inhibits the full insertion thereof in the opening 36 of the base 35 and the indexing movement of the indexing leg 21. By virtue of the present invention, increased accuracy for the replacement of the die 15 in the model 10 in the vertical plane has been provided.

We claim:

1. An assembly for prosthetic dentistry comprising:
   (a) a base, said base being formed with an indexing leg-receiving opening, a locator leg-receiving opening, and a debris-collecting opening, said debris-collecting opening communicating with said indexing leg-receiving opening;
   (b) a model secured to said base;
   (c) a die in said model removably attached to said base; and
   (d) a pin fixed in said die, said pin comprising an indexing leg projecting from said die and received by said indexing leg-receiving opening formed in said base, a locator leg projecting from said die and received by said locator leg-receiving opening formed in said base, and a retention member interconnecting said locator leg and said indexing leg and embodied in said die.

2. An assembly for prosthetic dentistry as claimed in claim 2 wherein said indexing leg is shorter than said locator leg.

3. An assembly for prosthetic dentistry as claimed in claim 2 wherein said indexing leg-receiving opening is shorter than said locator leg-receiving opening.

4. An assembly for prosthetic dentistry as claimed in claim 3 wherein said debris-collecting opening extends from said indexing leg-receiving opening to an exposed wall of said base.

5. An assembly for prosthetic dentistry as claimed in claim 3 wherein said debris-collecting opening extends from said indexing leg-receiving opening to a plane in which is disposed the tip of said locating leg.

6. A method of fabricating an assembly for prosthetic dentistry comprising the steps of:
   (a) forming a model;
   (b) embedding a pin in said model adjacent a tooth recess with an indexing leg of said pin and a locating leg of said pin projecting outwardly therefrom and with a retention member of said pin interconnecting said locator leg and said indexing leg embedded in said model;
   (c) placing a sleeve on the free end of said indexing leg;
   (d) forming a base for said model with said indexing leg and said locating leg and said sleeve embodied in said base and with the free end of said sleeve exposable; and
   (e) removing said sleeve from said base to form a debris-collecting opening communicating with the opening in said base receiving said indexing leg.

7. A method for fabricating an assembly for prosthetic dentistry as claimed in claim 6 and comprising the step of separating a section of said model having said pin embedded therein for providing a die separable from and replaceable in said model.

8. A method of fabricating an assembly for prosthetic dentistry as claimed in claim 7 wherein said sleeve is placed on the free end of said indexing leg so that the free end of said sleeve and the tip of locating pin extend an equal distance outwardly from said model.

9. A method of fabricating an assembly for prosthetic dentistry as claimed in claim 7 wherein said sleeve is placed on the free end of said indexing leg so that the tip of said sleeve and the tip of said locating pin are disposed in the same plane.

* * * * *